United States Patent
Duong et al.

(10) Patent No.: US 7,207,985 B2
(45) Date of Patent: Apr. 24, 2007

(54) DETACHABLE CRYOSURGICAL PROBE

(75) Inventors: Thach Duong, Garden Grove, CA (US); Sanford D. Damasco, Irvine, CA (US); David J. Battles, Kailua, HI (US); Paul W. Mikus, Irvine, CA (US); Jeffrey Kurtzer, San Clemente, CA (US)

(73) Assignee: Endocare, Inc., Irvine, CA (US)

( * ) Notice: Subject to any disclaimer, the term of this patent is extended or adjusted under 35 U.S.C. 154(b) by 218 days.

(21) Appl. No.: 10/603,883

(22) Filed: Jun. 25, 2003

(65) Prior Publication Data

US 2004/0267248 A1    Dec. 30, 2004

(51) Int. Cl.
*A61B 18/02* (2006.01)
*A61B 18/08* (2006.01)

(52) U.S. Cl. .............................. 606/20; 606/23; 606/27
(58) Field of Classification Search ............ 606/20–31; 607/88–92
See application file for complete search history.

(56) References Cited

U.S. PATENT DOCUMENTS

| | | | | |
|---|---|---|---|---|
| 3,913,581 A * | 10/1975 | Ritson et al. ................ 606/23 |
| 5,057,104 A * | 10/1991 | Chess .............................. 606/9 |
| 5,203,781 A * | 4/1993 | Bonati et al. .................. 606/15 |
| 5,344,418 A * | 9/1994 | Ghaffari ......................... 606/9 |
| 5,800,487 A | 9/1998 | Mikus ......................... 607/105 |
| 5,814,040 A * | 9/1998 | Nelson et al. ................. 606/9 |
| 5,820,626 A * | 10/1998 | Baumgardner .............. 606/13 |
| 5,830,208 A * | 11/1998 | Muller .......................... 606/9 |
| 5,910,104 A | 6/1999 | Doback ...................... 600/121 |
| 5,978,697 A | 11/1999 | Maytal ....................... 600/411 |
| 6,306,129 B1 * | 10/2001 | Little et al. ................... 606/23 |
| 6,767,346 B2 * | 7/2004 | Damasco et al. ............. 606/21 |
| 2002/0022832 A1 | 2/2002 | Mikus ......................... 606/20 |
| 2003/0055415 A1 | 3/2003 | Yu ............................... 606/21 |
| 2003/0055416 A1 | 3/2003 | Bui ............................. 606/21 |
| 2005/0010200 A1 * | 1/2005 | Damasco et al. ............. 606/21 |

* cited by examiner

*Primary Examiner*—A. Farah
(74) *Attorney, Agent, or Firm*—Lawrence N. Ginsberg

(57) ABSTRACT

A cryosurgical probe system includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly. The cryosurgical probe system includes the capability of providing return fluid flow.

36 Claims, 8 Drawing Sheets

DETACHABLE CRYOSURGICAL PROBE

BACKGROUND OF THE INVENTION

1. Field of the Invention

The present invention relates to cryosurgical probes and more particularly to a cryosurgical probe that is detachable and particularly useful with computerized tomography (CT) and other image-guided (radiological) applications.

2. Description of the Related Art

Cryosurgery involving the use of a cryosurgical probe assemblies typically involves the use of cryoprobes that are each attached to a handle that are, in turn, connected to a high-pressure fluid line with a quick-disconnect for attachment to a fluid source. There is an inherent problem with this type of system inasmuch as each cryosurgical probe assembly should be used only once due to sterilization and performance factors. Therefore, typically, the entire cryosurgical probe assembly and high-pressure fluid line must be discarded after that single use. Due to these sterilization/performance requirements there is a need to assure that the cryosurgical probe assembly may be rendered non-useable after a single-use.

Previous attempts to mitigate this problem have involved utilizing a disposable sheath over a cryosurgical probe. For example, U.S. Pat. No. 5,910,104, issued to J. D. Doback, III et al, discloses a disposable, sterilizable sheath for use on a closed loop Joule-Thomson cryosurgical probe, and the combination of the disposable sheath and the closed loop probe. The sheath is slipped over the probe, thereby separating the probe from the environment. The sheath has a grip that fits over the handle of the cryosurgical probe. The sheath has a hollow multi-lumen catheter shaped and sized to fit snugly over the cannula of the cryosurgical probe.

U.S. Pat. No. 6,306,129 B1, issued to Little et al, also discloses the use of a disposable sheath over a cryosurgical probe.

Similarly, U.S. Pat. Publication US 2002/0022832 A1, to Mikus et al, discloses a cryoprobe assembly that includes a cryoprobe and an outer sheath assembly detachably connected thereto.

Although cryosurgical probes have been very successfully used for treating prostate cancer their use has been somewhat limited for other applications such as liver, kidney, etc. because of the difficulty of imaging those body parts using ultrasound. Ultrasound is presently the preferred imaging instrumentality for prostate cryosurgery. It can be successfully used because the rectum, which is amenable to ultrasound imaging device insertion, is adjacent to the prostate. Thus, iceball formation can be effectively monitored. The liver, kidney, breast, etc. cannot be as conveniently monitored. Thus, it is desired that other imaging techniques be used. However, presently designed cryosurgical probes are not convenient with, for example, computerized tomography (CT) applications because the probe, including its handle and fluid line connection, are generally disposed along a single direction. This is problematic given the space considerations present with CT devices.

U.S. Pat. No. 5,978,697, issued to Maytal, et al, discloses an MRI-guided cryosurgical system. The Maytal system includes: (a) an MRI magnet for accommodating a patient, the MRI magnet having at least one opening for enabling access of a surgeon to the patient, the MRI magnet including at least one channel extending therethrough for receiving a line member of a surgical device; (b) a surgical device, including: (i) an operating member for operating the patient; (ii) a control member for controlling the operating member, the control member being positioned externally to the MRI room; and, (iii) a line member having a first end connectable to the operating member and a second end connectable to said control member, wherein at least a portion of the line member is received within the channel of the MRI magnet.

What is desired is a cryosurgical probe in which the operative portion of the cryosurgical probe is detachable. It is also desired that a cryosurgical probe be provided that can be used in conjunction with a variety of imaging devices.

SUMMARY OF THE INVENTION

In one broad aspect, the present invention is embodied as a cryosurgical probe system that includes a fluid supply line connectable at an inlet section to a source of cryogenic fluid; a fluid connector assembly securely connected to an outlet section of the fluid supply line for receiving fluid from the outlet section of the fluid supply line; and, a detachable cryosurgical probe detachably connectable to the fluid connector assembly. Unlike previous cryosurgical probe systems, the operative portion of the present system, i.e. the detachable cryosurgical probe, can be discarded after a single use. However, the fluid supply line and the connector assembly can be reused.

The cryosurgical probe system includes the capability of providing return fluid flow. This feature is provided by suitable passageways in the detachable cryosurgical probe and the fluid connector assembly.

In a broad aspect, the detachable cryosurgical probe includes a fluid delivery assembly, a return manifold assembly, an outer sheath, and a hub. The fluid delivery assembly has a proximal end section. The return manifold assembly is positioned over a portion of the fluid delivery assembly. The return manifold assembly provides a desired insulative air gap. The outer sheath is securely positioned over the return manifold assembly. The hub is securely positioned over the outer sheath and the return manifold assembly. The hub is for detachable connection to the fluid connector assembly of the detachable cryosurgical system. During operation, fluid is delivered through the fluid delivery assembly, through a Joule-Thomson (J-T) port defined at a distal end of the fluid delivery assembly and is returned through the return manifold assembly and delivered out of the cryosurgical probe. An insulative air gap is provided between the outer sheath and the return manifold at a control region of the outer sheath proximal to a distally located treatment region of the outer sheath.

The fluid connector assembly includes a cylindrical connector housing; a lock housing; a spacing element; a high pressure seal; a low pressure seal; and, a locking spring. The cylindrical connector housing has a radially extending boss securely attached to the outlet section of the fluid supply line. The connector housing has a fluid inlet conduit for receiving high pressure fluid from the fluid supply line and a fluid outlet conduit for transferring return fluid from the cryosurgical probe to the fluid supply line.

A lock housing is securely positioned within an axial opening of the connector housing. The lock housing has a cylindrical portion and a locking portion. A spacing element axially positions the lock housing relative to the connector housing and radially positions the detachable cryosurgical probe relative to the lock housing. A high pressure seal is positioned relative to the cryosurgical probe. The connector housing and the spacing element contain the high pressure fluid within the connector housing and enable the high pressure fluid to be delivered to the cryosurgical probe.

A low pressure seal is positioned relative to the cryosurgical probe. The spacing element and the lock housing prevent return fluid leakage. A locking spring is positioned in the locking portion of the lock housing to provide detachable engagement of the cryosurgical probe positioned therein.

The boss preferably extends at approximately 90 degrees from the axis of the connector housing. This enhances the capability of using this cryosurgical probe system with a CT device because the detachable cryosurgical probes, fluid connector assembly, and fluid supply line can be easily contained within the confines of the CT device.

DETAILED DESCRIPTION OF THE INVENTION

Figure 1:
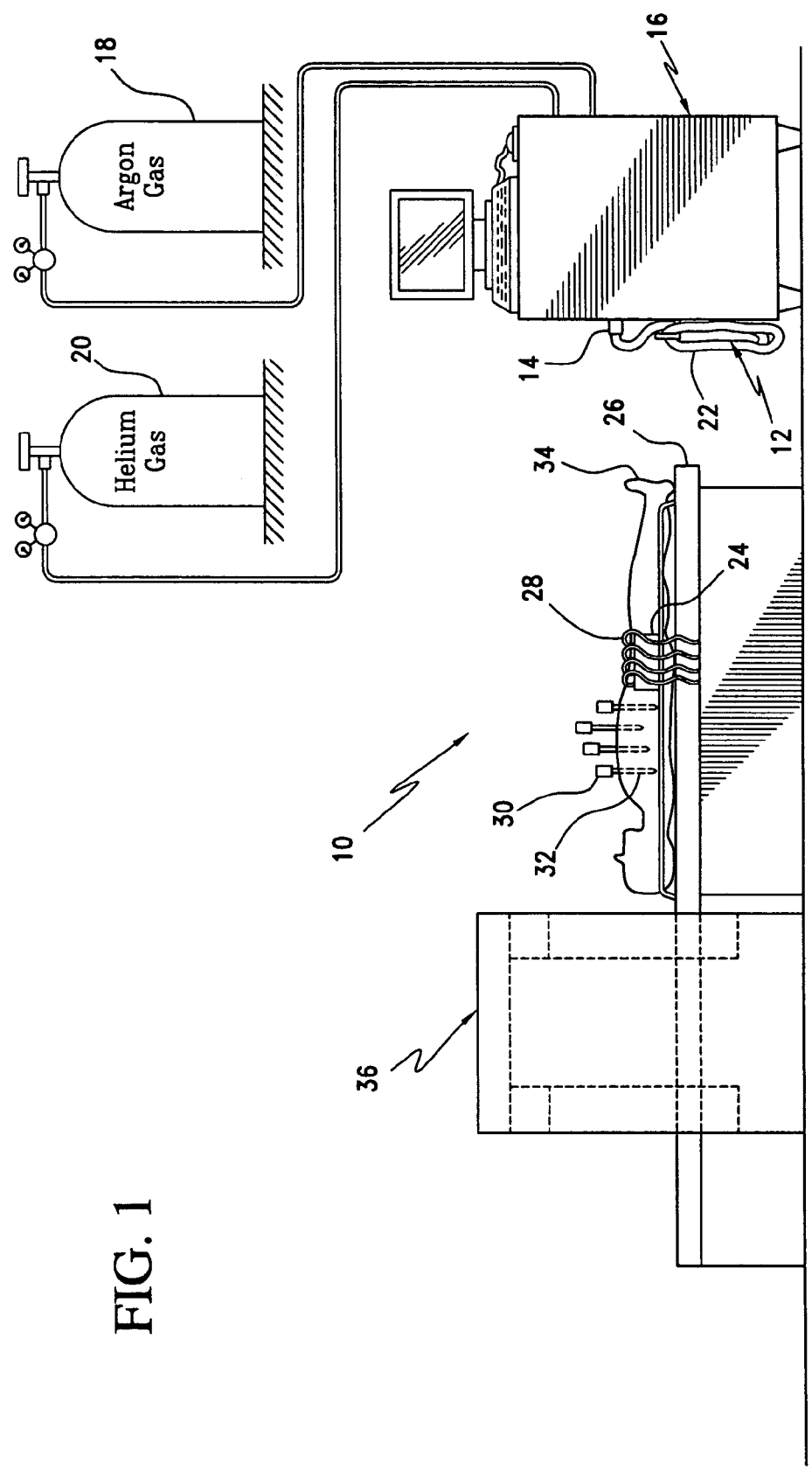
FIG. 1 is an overall system schematic of the cryosurgical probe system of the present invention, showing an environment with a patient positioned on a CT table prior to connection of the fluid lines and prior to being introduced into the CT device.

Referring now to the drawings and the characters of reference marked thereon, FIG. 1 illustrates a preferred embodiment of the cryosurgical probe system of the present invention, designated generally as 10. The cryosurgical probe system 10 includes a fluid supply line 12 that is connected at an inlet section 14 to a source 16 of cryogenic fluid. The fluid source 16 may be, for example, a cryosurgical system such as that manufactured by present assignee, Endocare, Inc., Irvine, Calif. Such a cryosurgical system typically utilizes argon gas from an argon gas source 18 to provide Joule-Thomson cooling of the cryosurgical probes. Heating of the cryosurgical probes is typically provided by a helium gas source 20 for providing a helium gas flow through the Joule-Thomson nozzle of the cryosurgical probe. This provides a heating effect. Such heating of the cryosurgical probes is provided to unstick the probes from the treated tissue for cryoprobe removal. Alternatively, other methods for warming may be used such as electrical heating via heated coils, microwave or RF heating.

The fluid supply line 12 preferably includes a manifold-system hose 22 for providing a connection from the source 16 to a manifold 24. The manifold 24 may be connected to a rail or otherwise to a CT table 26. Manifold-fluid connector assembly hoses 28 of the fluid supply line 12 provide fluid connections between fluid connector assemblies 32 and the manifold 24. The fluid connector assemblies 32 provide attachment to the detachable cryosurgical probes 32.

FIG. 1 illustrates a patient 34 positioned on a CT table 26 adjacent to a CT device 36. The cryosurgical probes 32 have been inserted in treatment zones for cryosurgical treatment. The hoses 28 are not yet connected to the manifold 24. It is assumed that prior to probe insertion shown in FIG. 1 that the tumor location has been confirmed under imaging guidance (e.g. CT, ultrasound, etc.).

Figure 2:
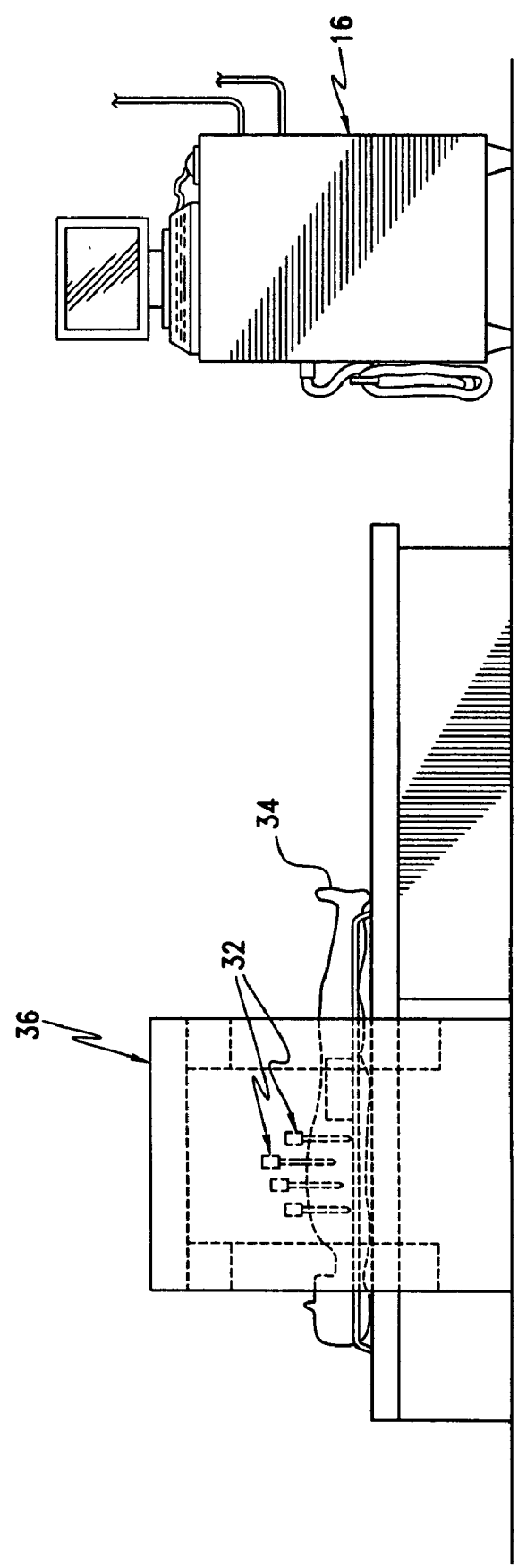
FIG. 2 is an overall system schematic showing a patient introduced into the CT device but prior to cryosurgical treatment.

Referring now to FIG. 2, the patient 34 is introduced into the imaging section of the CT device 36 and scans are taken with the cryosurgical probes 32 inserted. These initial scans are made to assure that the tips of the cryosurgical probes 32 are properly positioned per a treatment plan.

Figure 3:
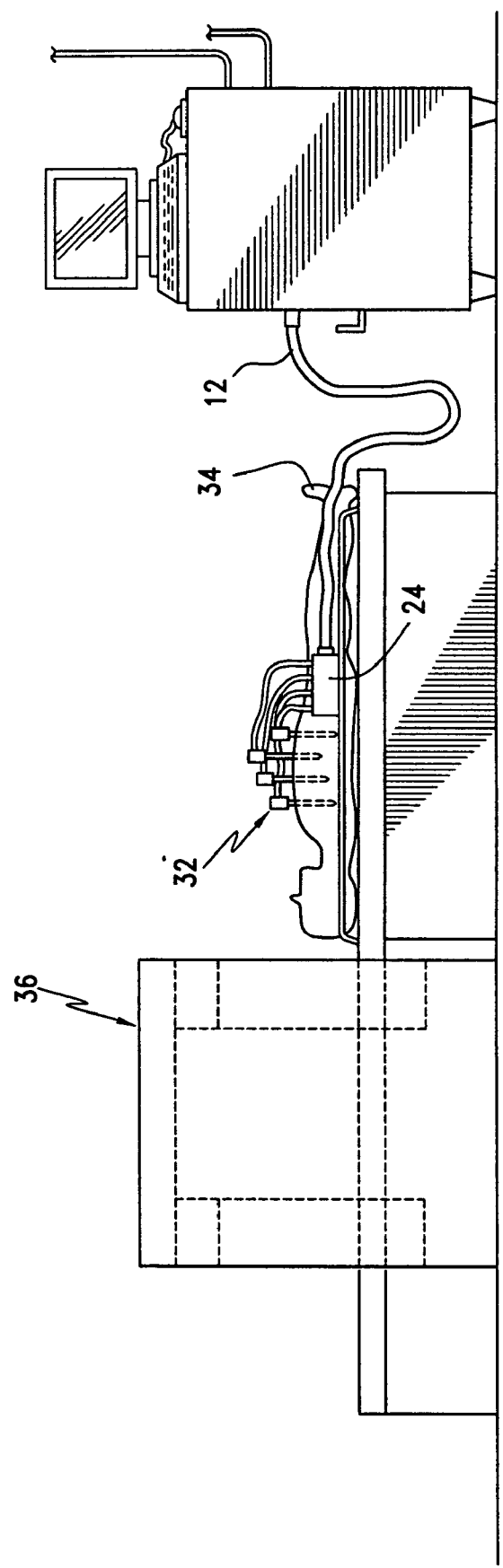
FIG. 3 shows the patient positioned away from the CT device and the cryosurgical probes attached to a manifold in preparation for cryosurgery.

Referring now to FIG. 3, the patient 34 is shown positioned away from the imaging section of the CT device 36 and the cryosurgical probes 32 are attached to the manifold 24 in preparation for cryosurgery.

Figure 4:
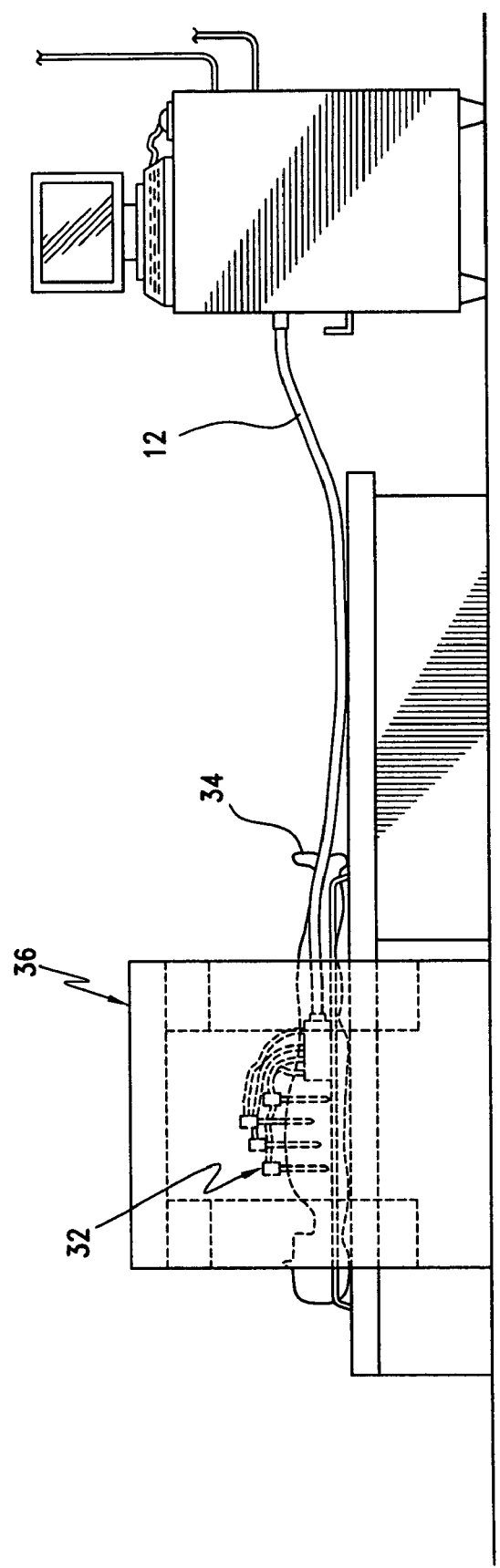
FIG. 4 shows the patient introduced to the CT device and cryosurgery being performed under CT scanning guidance.

As shown in FIG. 4, the patient is then again introduced to the device 36 and cryosurgery is performed under CT scanning. This allows for the monitoring of the iceballs formed during this procedure. There are typically two freeze-thaw cycles included in a cryosurgical treatment.

Figures 5, 6:
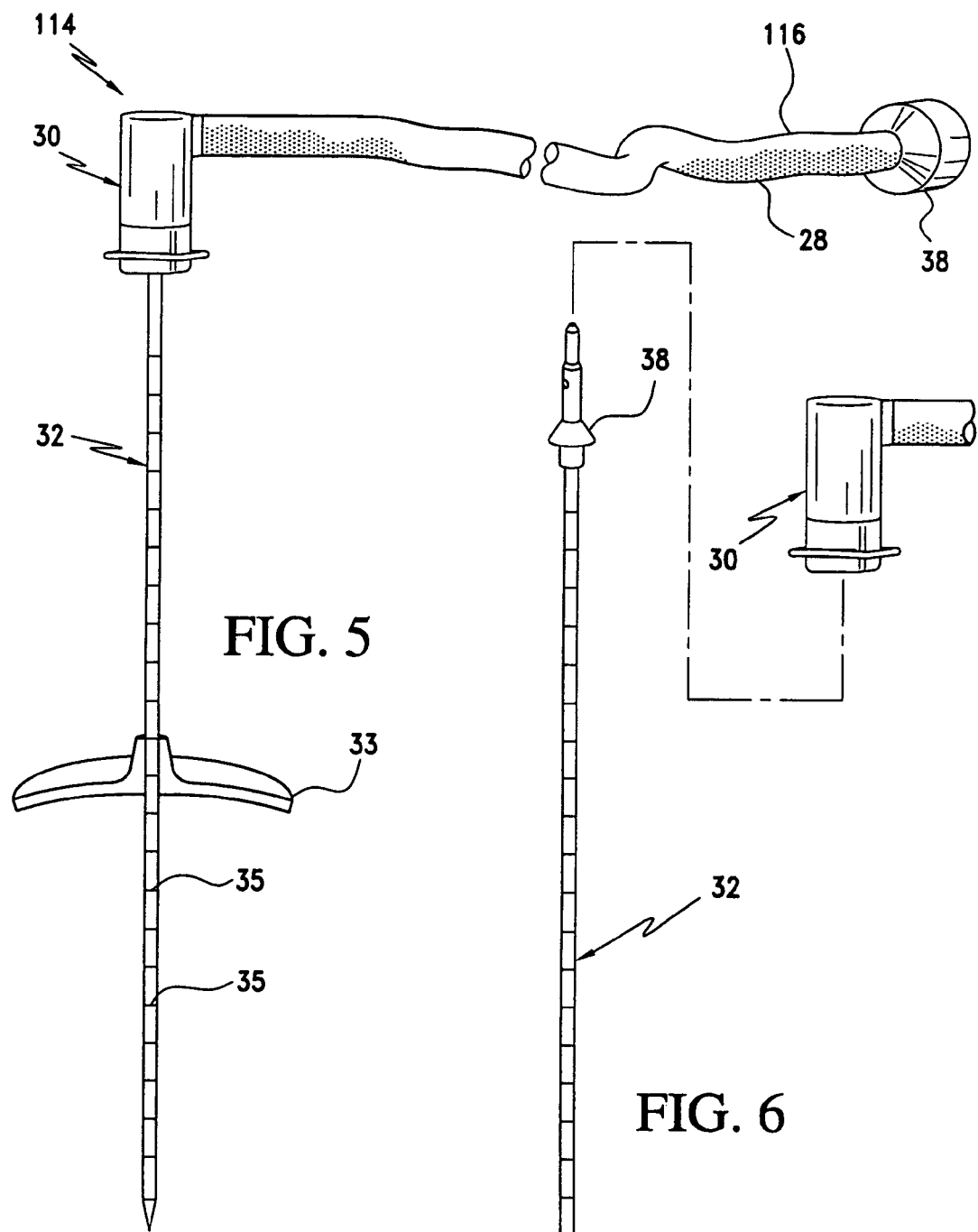
FIG. 5 is a perspective illustration of the cryosurgical probe inserted within the connector assembly.
FIG. 6 is a perspective illustration of the cryosurgical probe detached from the connector assembly.

Referring now to FIG. 5, a cryosurgical probe 32 is shown inserted within its connector assembly 30. A manifold-fluid connector assembly hose 28 is shown with appropriate connector 38 for connection to the manifold 24. The cryosurgical probe 32 preferably includes a slideable wedge element 33 that can be used as a marker for assuring that the correct depth of the cryosurgical probe 32 is maintained. Furthermore, the bottom of the wedge element 33 contacts the body of the patient 34 to decrease the probability of accidental translation of the cryosurgical probe 32. Spaced markings 35 may be provided on the outer surface of the cryosurgical probe 32. These markings 35 may be, for example, at 1 cm intervals.

Referring now to FIG. 6, the cryosurgical probe 32 is shown detached from its connector assembly 30. As can be seen in this figure, and described in detail below, the detachable cryosurgical probe 32 includes a radially extending hub 38 that provides attachment to the connector assembly 30.

Figure 7:
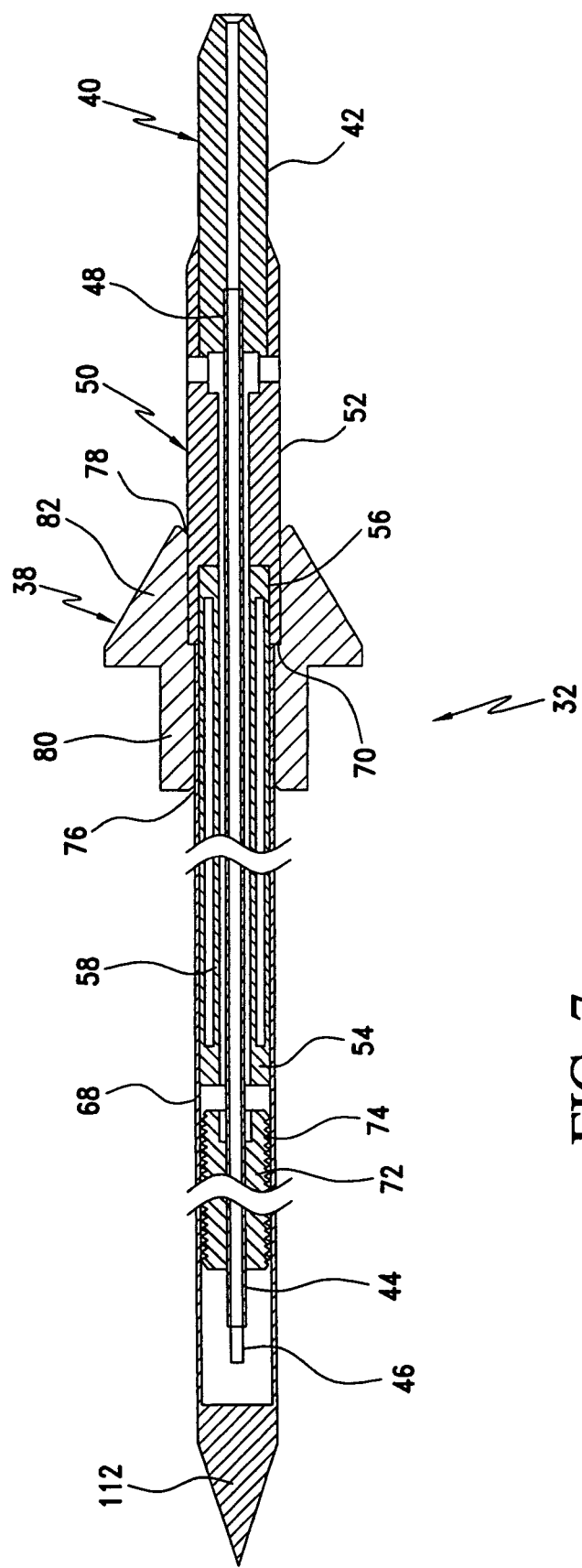
FIG. 7 is a cross-sectional view of the cryosurgical probe.

Referring now to FIG. 7, a preferred embodiment of the cryosurgical probe 32 is illustrated. The cryosurgical probe 32 includes a fluid delivery assembly, designated generally as 40. The fluid delivery assembly 40 includes a high pressure stem 42, an extension tube 44 and an orifice tube 46. The high pressure stem 42 has a proximal end section that receives high pressure fluid from the fluid connector assembly 30. The extension tube 44 is welded, at a first end 48, to the high pressure stem. The extension tube 44 is in fluid communication with the high pressure stem 42. The orifice tube 46 is secured to a second end of the extension tube 44. The orifice tube 46 is in fluid communication with the extension tube 44. The orifice tube 46 comprises a Joule-Thomson (J-T) port at a distal end thereof.

The cryosurgical probe 32 includes a return manifold assembly, designated generally as 50. The return manifold assembly 50 includes a low pressure stem 52 and a vacuum tube 54. The low pressure stem 52 is positioned about an outer surface of the high pressure stem 40 and is securely connected to the high pressure stem 40. It may be secured via threads and adhesive or by welding. The vacuum tube 54 is secured at an end 56 to the low pressure stem 52. The vacuum tube 54 has a desired insulative air gap 58 formed therein. The air gap 58 provides selected non-cooling areas of the cryosurgical probe 32.

An outer sheath 68 is securely positioned over the return manifold assembly 50. The outer sheath 68 is a cylindrical tube preferably formed of stainless steel which provides the desired heat transfer characteristics. The outer sheath 68 is welded to the low pressure stem 52 at location 70. It is pointed at its closed distal end to provide insertion to the treatment area tissue. The outer sheath 68 includes a cylindrical collector 72 having external threads 74 that cooperate with the cylindrical tube 68 to guide the return fluid from the J-T port 46 to the vacuum tube 54, as will be explained below in detail.

The hub 38 is securely positioned over the outer sheath 68 and the return manifold assembly 50. The hub 38 is securely connected at weld location 76 to the outer sheath 68 and at weld location 78 to the low pressure stem 52. The hub 38 includes a cylindrical portion 80 and a tapered extension 82 extending therefrom. The tapered extension 82 has a radial extending portion. The cylindrical portion 80 is securely attached to the outer sheath 68 and the tapered extension is securely attached to the low pressure stem 52.

Figure 8:
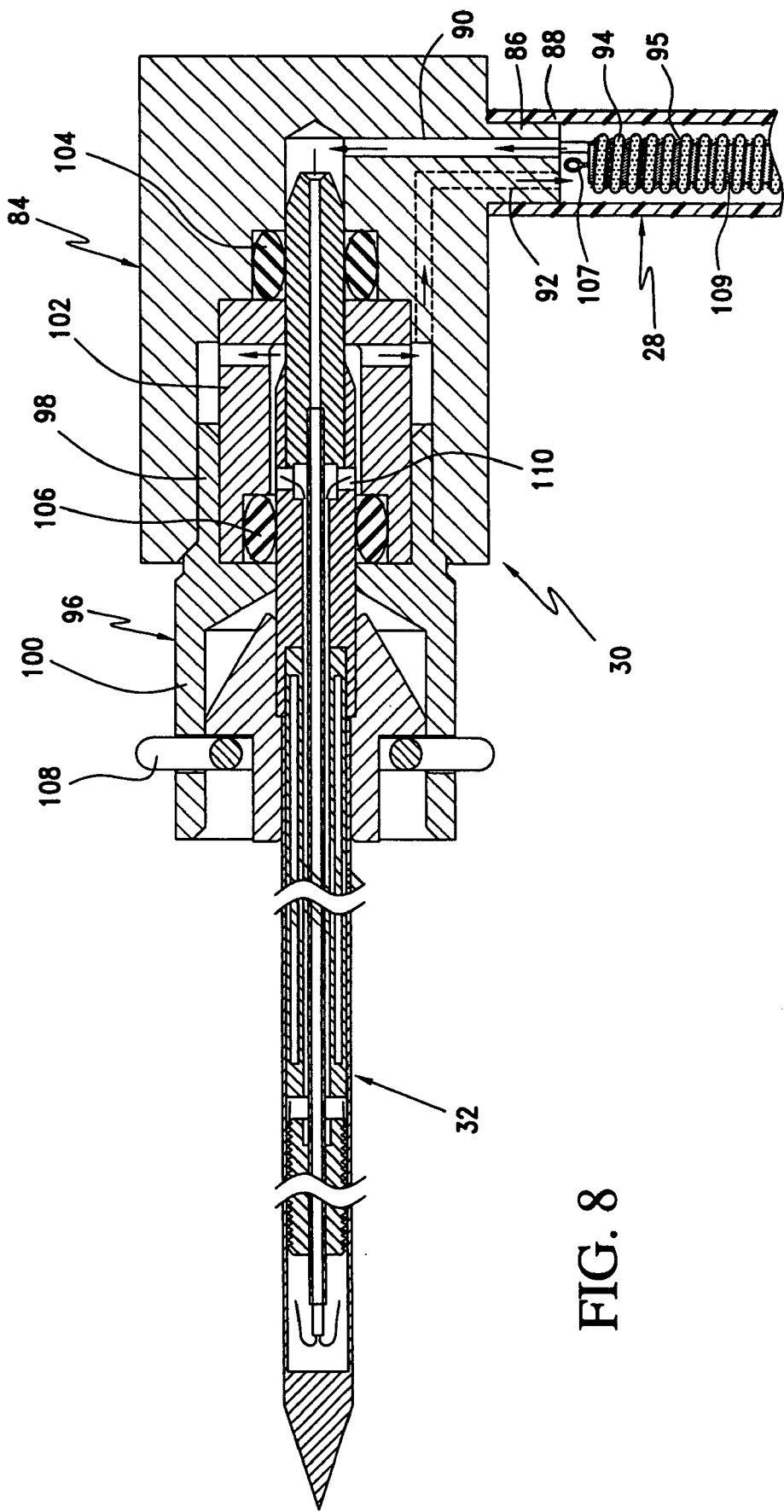
FIG. 8 is a cross-sectional view of the cryosurgical probe inserted within the connector assembly.

Referring now to FIG. 8, the cryosurgical probe 32 is shown inserted into the connector assembly 30. The connector assembly 30 includes a substantially cylindrical connector housing 84 having a radially extending boss 86 securely attached to the outlet section 88 of the manifold-fluid connector assembly hose 28 of the fluid supply line 12. The connector housing 84 has a fluid inlet conduit 90 for receiving high pressure fluid from the fluid supply line 12 and a fluid outlet conduit 92 for transferring return fluid from the cryosurgical probe 32 to the fluid supply line 12. The connector housing 84 has a central axis parallel to the cryosurgical probe 32. The radially extending boss 86 is at substantially 90 degrees relative to that central axis to maintain the supply line closer to the patient, which is advantageous for CT related applications due to the space limitations. A cryostat 94 is positioned in the manifold-fluid connector assembly hose 28. The cryostat 94 preferably has fins 95.

The fluid connector assembly includes a lock housing 96, which is securely positioned within an axial opening of the connector housing 84. The lock housing 96 has a cylindrical portion 98 and a locking portion 100. A spacing element 102 axially positions the lock housing 100 relative to the connector housing 84 and radially positions the detachable cryosurgical probe 32 relative to the lock housing 96.

A high pressure seal 104 is positioned relative to the cryosurgical probe 32, the connector housing 84 and the spacing element 102 to contain the high pressure fluid within the connector housing 84 and enable the high pressure fluid to be delivered to the cryosurgical probe 32.

A low pressure seal 106 is positioned relative to the cryosurgical probe 32, the spacing element 102, and the lock housing 100 to prevent return fluid leakage.

A locking spring 108 is positioned in the locking portion 100 of the lock housing 96 to provide detachable engagement of a cryosurgical probe positioned therein.

Positioned within the connector assembly 30 is a thermocouple 107. The thermocouple 107 is contained within a thermocouple housing tube 109 for providing temperature data. The thermocouple housing tube 109 supports the cryostat 94.

During operation, with the cryosurgical probe positioned within the connector assembly 30, cryogenic fluid originating from the argon tank 18 flows through the manifold-fluid connector assembly hose 28 within the cryostat 94 and through the conduit 90 in the connector housing 84. The flow is re-directed approximately 90 degrees, flows through the central passageway in the high pressure stem 42, through the extension tube 44, through the orifice tube 46, and out of the J-T port.

After being expelled from the J-T port the return fluid is directed between the threads 74 of the cylindrical collector 72 and the outer sheath 68. (The cylindrical collector 72 is not threaded into the outer sheath 68 and therefore the threads 74 provide a path for fluid flow.) The return flow then travels in the space between the inner surface of the vacuum tube 54 and the outer surface of the extension tube 44. It then flows through openings 110 in the low-pressure stem 52 through the spacing element 102 and through the fluid outlet conduit 92 in the connector housing 84. The return fluid is then expelled through the manifold-fluid connector assembly hose 28.

The cryosurgical probe 32 preferably has a length in a broad range of 2–20 inches, preferably about 5–15 inches. A preferred length is about 7 inches, which is useful far CT applications In the device illustrated the cryosurgical probe 32 is shown with a pointed tip 112 to provide insertion into the patient's tissue for the desired application. However, it is understood that the tip may be blunt, depending on the application. For example, for certain applications direct insertion is desirable. For other applications, insertion via a cannula/introducer is preferred.

Although application of this device utilizing CT guidance has been discussed, the cryosurgical probe 32 may be used with a variety of guidance tools, such as MRI and ultrasound. In one preferred implementation ultrasound is used for initial guidance, followed up with CT for final confirmation.

Although the present invention has been discussed above with respect to a cryosurgical probe having with a rigid outer sheath, the cryosurgical probe may be made to be malleable by including at least one malleable segment thereon. Malleable segments are formed of material that permit reshaping and bending to reposition the ablating surface for greater ablation precision. An example of a cryosurgical probe having malleable characteristics is disclosed and claimed in our co-pending patent application Ser. No. 09/957,337, Pub. No. US 2003/0055415 A1, filed on Sep. 20, 2001 entitled Malleable Cryosurgical Probe, incorporated in its entirety herein by reference.

One method for providing malleable characteristics includes providing a malleable shaft with a bellows portion. Our co-pending patent application Ser. No 10/057,033, Pub. No. US 2003/0055416 A1, filed on Jan. 23, 2002 entitled Cryosurgical Probe With Bellows Shaft, incorporated in its entirety herein by reference, discloses use of a bellows portion for providing the necessary reshaping and bending.

Although the cryosurgical probe has been shown as having approximately a 90 degree extension from the point where the manifold-fluid connector assembly hoses 28 connect it is understood that this angle can vary depending on the desired application. The desired connection angle may be, for example, in a broad range of from 0 degrees to 180 degrees (i.e. there may not be a bend). A preferred range is about 80 degrees to about 140 degrees.

If the detachable cryosurgical probe is utilized in combination with ultrasound the outer sheath may have an echogenic coating with, for example, a porous microstructure having the ability to trap microscopic air bubbles. This creates thousands of highly efficient ultrasound reflectors on the surface of the sheath.

Figure 9:
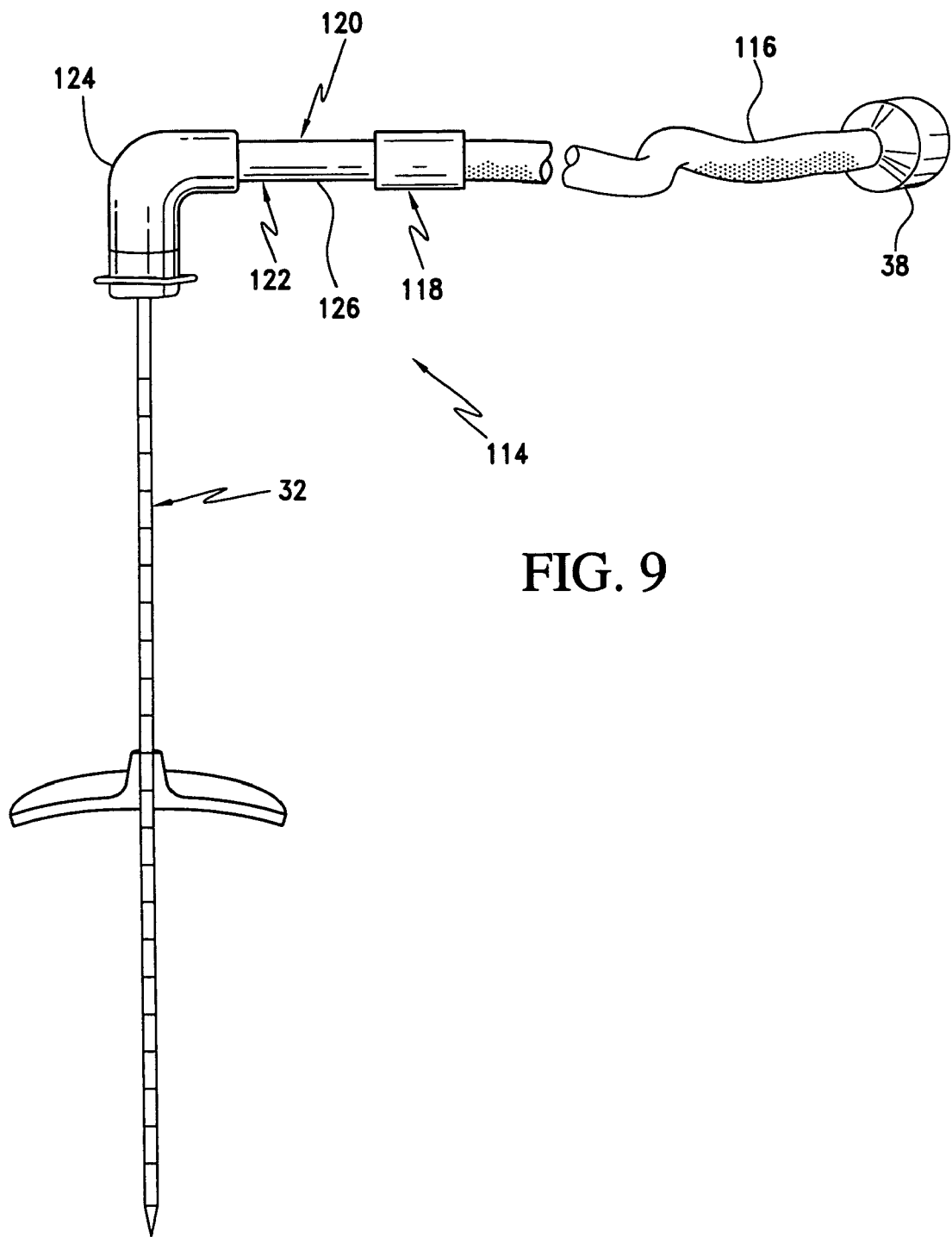
FIG. 9 shows an alternative embodiment of the cryosurgical probe in which a rigid curved portion is utilized and a connector assembly positioned proximal to the rigid curved portion.

Referring now to FIG. 9, another embodiment of the cryosurgical probe system is illustrated, designated generally as 114. In this embodiment, a fluid supply line 116 is connectable at an inlet section to a source of cryogenic fluid (not shown). A fluid connector assembly 118 is securely connected to an outlet section of the fluid supply line 116 for receiving fluid from the outlet section of the fluid supply line 116. A detachable cryosurgical probe 120 is detachably connectable to the fluid connector assembly 118. The cryosurgical probe 120 receives fluid from the fluid connector assembly 118. In this embodiment, the cryosurgical probe 120 includes an angled extension assembly 122. Angled extension assembly 122 includes an angled portion 124 and extension portion 126. The angled extension assembly 122, in this embodiment, provides the ability to connect the fluid supply line 116 to the cryosurgical probe 120 without effecting the probe position within the patient (which has already been confirmed under image guidance).

Thus, while the preferred embodiments of the devices and methods have been described in reference to the environment in which they were developed, they are merely illustrative of the principles of the invention.

For example, the use of a manifold-system hose 22 and manifold 24 may not be included. In such instance, for example, a manifold-fluid connector assembly hose 28 with connector 38 would be replaced with a fluid supply line that connects the connector assembly 30 directly at an inlet section 14 to a source 16 of cryogenic fluid.

Further, although the cryostat 94 has been shown positioned within the manifold-fluid connector assembly hose 28 it may be positioned in other locations, notably, for example, in the manifold 24 or within the source 16.

Although the cryosurgical probe system is particularly advantageous for radiological applications it is also advantageous for many other types of ablation applications, such as prostate cryosurgery and other operating room based procedures.

Other embodiments and configurations may be devised without departing from the spirit of the invention and the scope of the appended claims.

The invention claimed is:

1. A cryosurgical probe system, comprising:
   a. a fluid supply line connectable at an inlet section to a source of cryogenic fluid;
   b. a fluid connector assembly securely connected to an outlet section of said fluid supply line for receiving fluid from said outlet section of said fluid supply line; and,
   c. a detachable cryosurgical probe detachably connectable to said fluid connector assembly, said cryosurgical probe for receiving fluid from said fluid connector assembly and manipulating said fluid to provide suitable temperatures for cryosurgical ablation, wherein said cryosurgical probe comprises a bellows portion and includes a probe return fluid flow passageway, said fluid connector assembly includes a connector assembly return fluid flow passageway in fluid communication with said probe return fluid flow passageway, and said fluid supply line includes a supply line return fluid flow passageway in fluid communication with said connector assembly return fluid flow passageway.

2. The cryosurgical probe system of claim 1, wherein said detachable cryosurgical probe, comprises:
   a. a fluid delivery assembly having a proximal end section;
   b. a return manifold assembly positioned over a portion of said fluid delivery assembly; said return manifold assembly providing a desired insulative air gap;
   c. an outer sheath securely positioned over said return manifold assembly; and,
   d. a hub securely positioned over said outer sheath and said return manifold assembly, said hub for detachable connection to a fluid connector assembly of a detachable cryosurgical system,
   wherein during operation fluid is delivered through said fluid delivery assembly, through a Joule-Thomson (J-T) port defined at a distal end of said fluid delivery assembly and is returned through said return manifold assembly and delivered out of said cryosurgical probe, an insulative air gap being provided between said outer sheath and said return manifold at a control region of said outer sheath proximal to a distally located treatment region of said outer sheath.

3. The cryosurgical probe system of claim 2, wherein said fluid delivery assembly comprises:
   a. a high pressure stem for receiving high pressure fluid from the fluid connector assembly;
   b. an extension tube secured, at a first end, to said high pressure stem, said extension tube being in fluid communication with said high pressure stem; and,
   c. an orifice tube secured to a second end of said extension tube, said orifice tube being in fluid communication with said extension tube, said orifice tube having said J-T port at a distal end thereof.

4. The cryosurgical probe system of claim 3, wherein said return manifold assembly comprises:
   a. a low pressure stem positioned about an outer surface of said high pressure stem, said low pressure stem being securely connected to said high pressure stem; and,
   b. a vacuum tube secured at a first end to said low pressure stem, said vacuum tube having said desired insulative air gap formed therein, a portion of the return fluid flow passageway being provided between a space formed between an inner surface of said vacuum tube and an outer surface of said extension tube,
   another portion of the return fluid flow passageway being provided between a space formed between an inner surface of said low pressure stem and an outer surface of said extension tube, said low pressure stem further including at least one opening to deliver return fluid to said fluid connector assembly.

5. The cryosurgical probe system of claim 4, wherein said outer sheath, comprises:
   a cylindrical tube having a closed distal end.

6. The cryosurgical probe system of claim 5, wherein said hub, comprises:
   a. a cylindrical portion; and,
   b. a tapered extension extending from said cylindrical portion, said tapered extension having a radial extending portion, wherein said cylindrical portion is securely attached to said outer sheath and said tapered extension is securely attached to said low pressure stem.

7. The cryosurgical probe system of claim 6, wherein said sheath further includes a cylindrical collector having external threads that cooperate with said cylindrical tube to guide the return fluid from the J-T port to said vacuum tube.

8. The cryosurgical probe system of claim 1, wherein said detachable cryosurgical probe has a total length in a range of 2–20 inches.

9. The cryosurgical probe system of claim 1, wherein said detachable cryosurgical probe has a total length in a range of 5–15 inches.

10. The cryosurgical probe system of claim 1, wherein said fluid connector assembly comprises:
 a. a substantially cylindrical connector housing having a radially extending boss securely attached to said outlet section of said fluid supply line, said connector housing having a fluid inlet conduit for receiving high pressure fluid from said fluid supply line and a fluid outlet conduit for transferring return fluid from said cryosurgical probe to said fluid supply line;
 b. a lock housing securely positioned within an axial opening of said connector housing, said lock housing having a cylindrical portion and a locking portion;
 c. a spacing element for axially positioning said lock housing relative to said connector housing and radially positioning said detachable cryosurgical probe relative to said lock housing;
 d. a high pressure seal positioned relative to said cryosurgical probe, said connector housing and said spacing element to contain the high pressure fluid within the connector housing and enable the high pressure fluid to be delivered to said cryosurgical probe;
 e. a low pressure seal positioned relative to said cryosurgical probe, said spacing element, and said lock housing to prevent return fluid leakage; and,
 f. a locking spring positioned in said locking portion of said lock housing to provide detachable engagement of a cryosurgical probe positioned therein.

11. The cryosurgical probe system of claim 10, wherein said connector housing and said radially extending boss are at substantially 90 degrees relative to each other.

12. The cryosurgical probe system of claim 10, wherein said connector housing and said radially extending boss are positioned at an angle from between about 0 degrees and 180 degrees relative to each other.

13. The cryosurgical probe system of claim 10, wherein said connector housing and said radially extending boss are positioned at an angle from between about 80 degrees and 140 degrees relative to each other.

14. The cryosurgical probe system of claim 10, wherein said fluid supply line comprises a cryostat positioned therein for delivering fluid from the fluid supply line to said fluid connector assembly.

15. The cryosurgical probe system of claim 1, wherein said outlet section of said fluid supply line and a longitudinal axis of said cryosurgical probe are at substantially 90 degrees relative to each other.

16. The cryosurgical probe system of claim 1, wherein said outlet section of said fluid supply line and a longitudinal axis of said cryosurgical probe are positioned at an angle from between about 0 degrees and 180 degrees relative to each other.

17. The cryosurgical probe system of claim 1, wherein said outlet section of said fluid supply line and a longitudinal axis of said cryosurgical probe are positioned at an angle from between about 80 degrees and 140 degrees relative to each other.

18. The cryosurgical probe system of claim 1, wherein said cryogenic fluid comprises argon.

19. The cryosurgical probe system of claim 1, wherein said fluid supply line is connectable to a fluid source of a type that warms while undergoing Joule-Thomson expansion.

20. The cryosurgical probe system of claim 1, further comprising an ultrasound system for guidance.

21. The cryosurgical probe system of claim 1, further comprising an MRI system for guidance.

22. The cryosurgical probe system of claim 1, wherein said detachable cryosurgical probe further includes means for warming said cryosurgical probe.

23. The cryosurgical probe system of claim 1, wherein said detachable cryosurgical probe further includes means for warming, said means for warming comprising electrical heating means.

24. The cryosurgical probe system of claim 1, wherein said detachable cryosurgical probe further includes means for warming, said means for warming comprising RF heating means.

25. The cryosurgical probe system of claim 1, wherein said fluid connector assembly comprises a thermocouple secured therein for providing temperature data.

26. The cryosurgical probe system of claim 1, wherein said detachable cryosurgical probe comprises an outer sheath having an echogenic coating.

27. The cryosurgical probe system of claim 1, wherein said detachable cryosurgical probe comprises a malleable segment.

28. A cryosurgical probe system, comprising:
 a. a fluid supply line;
 b. a fluid connector assembly securely connected to said fluid supply line for receiving fluid from said fluid supply line; and,
 c. a detachable cryosurgical probe detachably connectable to said fluid connector assembly, said cryosurgical probe for receiving fluid from said fluid connector assembly and manipulating said fluid to provide suitable temperatures for ablation, wherein
 said cryosurgical probe comprises a bellows portion and includes a probe return fluid flow passageway, said fluid connector assembly includes a connector assembly return fluid flow passageway in fluid communication with said probe return fluid flow passageway, and said fluid supply line includes a supply line return fluid flow passageway in fluid communication with said connector assembly return fluid flow passageway.

29. A detachable cryosurgical probe for connection to a fluid connector assembly of a detachable cryosurgical system, comprising:
 a. a fluid delivery assembly having a proximal end section;
 b. a return manifold assembly positioned over a portion of said fluid delivery assembly;
  said return manifold assembly providing a desired insulative air gap;
 c. an outer sheath securely positioned over said return manifold assembly; and,
 d. a hub securely positioned over said outer sheath and said return manifold assembly, said hub for detachable connection to a fluid connector assembly of a detachable cryosurgical system,
 wherein during operation fluid is delivered through said fluid delivery assembly, through a Joule-Thomson (J-T) port defined at a distal end of said fluid delivery assembly and is returned through said return manifold assembly and delivered out of said cryosurgical probe, an insulative air gap being provided between said outer sheath and said return manifold at a control region of said outer sheath proximal to a distally located treatment region of said outer sheath.

30. The detachable cryosurgical probe of claim 29, wherein said fluid delivery assembly comprises:

a. a high pressure stem for receiving high pressure fluid from the fluid connector assembly;
b. an extension tube secured, at a first end, to said high pressure stem, said extension tube being in fluid communication with said high pressure stem; and,
c. an orifice tube secured to a second end of said extension tube, said orifice tube being in fluid communication with said extension tube, said orifice tube having said J-T port at a distal end thereof.

31. The detachable cryosurgical probe of claim 30, wherein said return manifold assembly comprises:
a. a low pressure stem positioned about an outer surface of said high pressure stem, said low pressure stem being securely connected to said high pressure stem; and,
b. a vacuum tube secured at a first end to said low pressure stem, said vacuum tube having said desired insulative air gap formed therein, a portion of the return fluid flow passageway being provided between a space formed between an inner surface of said vacuum tube and an outer surface of said extension tube,
another portion of the return fluid flow passageway being provided between a space formed between an inner surface of said low pressure stem and an outer surface of said extension tube, said low pressure stem further including at least one opening to deliver return fluid to said fluid connector assembly.

32. The detachable cryosurgical probe of claim 29, wherein said outer sheath, comprises:
a cylindrical tube having a closed distal end.

33. The detachable cryosurgical probe of claim 29, wherein said hub, comprises:
a. a cylindrical portion; and,
b. a tapered extension extending from said cylindrical portion, said tapered extension having a radial extending portion, wherein said cylindrical portion is securely attached to said outer sheath and said tapered is securely attached to said low pressure stem.

34. The detachable cryosurgical probe of claim 29, wherein said sheath further includes a cylindrical collector having external threads that cooperate with said cylindrical tube to guide the return fluid from the J-T port to said vacuum tube.

35. The detachable cryosurgical probe of claim 29, having a total length in a range of 2–20 inches.

36. The detachable cryosurgical probe of claim 29, having a total length in a range of 5–15 inches.

* * * * *